US009345550B2

(12) United States Patent  
Richter et al.

(10) Patent No.: US 9,345,550 B2  
(45) Date of Patent: May 24, 2016

(54) METHOD AND SYSTEM FOR CHARACTERIZING STIMULUS SITES AND PROVIDING IMPLANT GUIDANCE

(71) Applicant: Pacesetter, Inc., Sunnyvale, CA (US)

(72) Inventors: Sergio Richter, Leipzig (DE); Philipp Sommer, Markkleeberg (DE); Edith Arnold, San Francisco, CA (US); Hoda Razavi, San Jose, CA (US); Yelena Nabutovsky, Mountain View, CA (US); Fujian Qu, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 98 days.

(21) Appl. No.: 14/069,209

(22) Filed: Oct. 31, 2013

(65) Prior Publication Data

US 2015/0119966 A1    Apr. 30, 2015

(51) Int. Cl.  
*A61B 19/00* (2006.01)  
*A61N 1/362* (2006.01)  
*A61N 1/05* (2006.01)  
*A61N 1/37* (2006.01)

(52) U.S. Cl.  
CPC ............. *A61B 19/50* (2013.01); *A61N 1/3627* (2013.01); *A61N 1/056* (2013.01); *A61N 1/37* (2013.01)

(58) Field of Classification Search  
None  
See application file for complete search history.

(56) References Cited

U.S. PATENT DOCUMENTS

| | | | |
|---|---|---|---|
| 6,978,184 B1 | 12/2005 | Marcus | |
| 7,499,743 B2 | 3/2009 | Vass | |
| 7,787,951 B1 | 8/2010 | Min | |
| 8,106,905 B2 | 1/2012 | Markowitz | |
| 2008/0281195 A1* | 11/2008 | Heimdal | 600/437 |
| 2010/0191100 A1* | 7/2010 | Anderson et al. | 600/424 |
| 2011/0213260 A1 | 9/2011 | Keel | |

OTHER PUBLICATIONS

R. Nezafat, et al. "Coronary magnetic resonance vein imaging: imaging contrast, sequence, and timing," Magnetic resonance in medicine: official journal of the Society of Magnetic resonance in Medicine/Society of Magnetic Resonance in Medicine, vol. 58, No. 6, pp. 1196-206, Dec. 2007.

J.P. Singh, et al, "The Coronary venous anatomy: a segmental approach to aid cardiac resynchronization therapy." Journal of the American College of Cardiology, vol. 46, No. 1, pp. 68-74, Jul. 2005.

(Continued)

*Primary Examiner* — Brian T Gedeon  
*Assistant Examiner* — Ankit Tejani  
(74) *Attorney, Agent, or Firm* — Theresa A. Raymer

(57) ABSTRACT

A method and system for characterizing an accessibility of potential left ventricular stimulus sites in connection with surgical planning for transvenous implant of a cardiac medical lead in or near a heart of a patient are provided. The method and system include obtaining image data representative of a coronary venous system for the heart of the patient to receive the lead. The method and system generate a venous map, based on the image data, representative of venous pathways for the heart of the patient. The method and system analyze the venous map to identify pathway features of interest (PFOI) within at least one select region of the venous pathways. The method and system assign scores to the PFOI based on at least one of predetermined feature-complexity relations or physician-entered complexity updates. The method and system display treatment planning information to a user based on the scores.

22 Claims, 7 Drawing Sheets

(56) References Cited

OTHER PUBLICATIONS

M. Centonze, et al. "Cardiac Veins and Pulmonary Veins." Clinical Applications of Cardiac CT, pp. 185-200, 2012.

P.M. O'Flynn, et al. "Methods for three-dimensional geometric characterization of the arterial vasculature." Annals of Biomedical Engineering, vol. 35, No. 8, pp. 1368-1381, Aug. 2007.

* cited by examiner

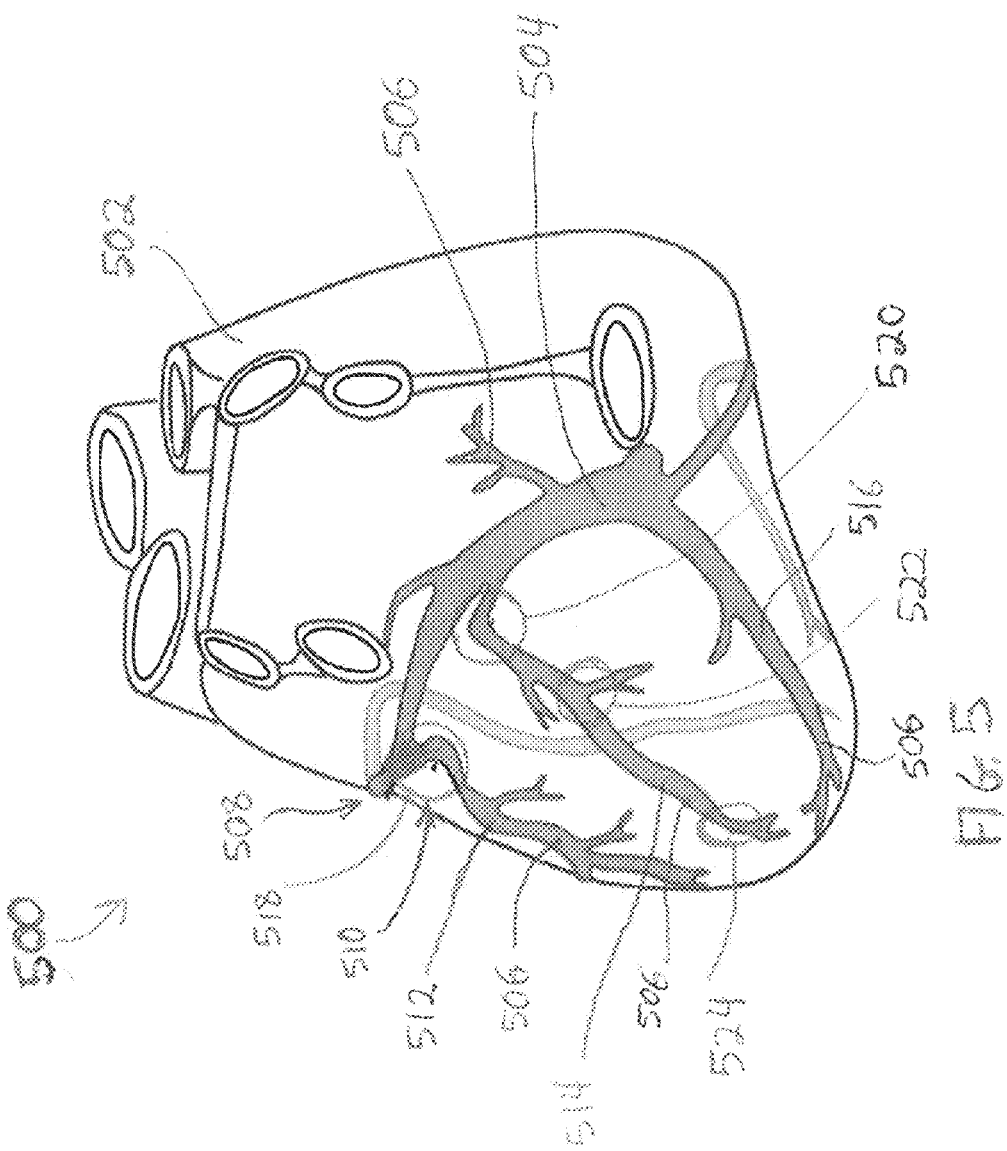

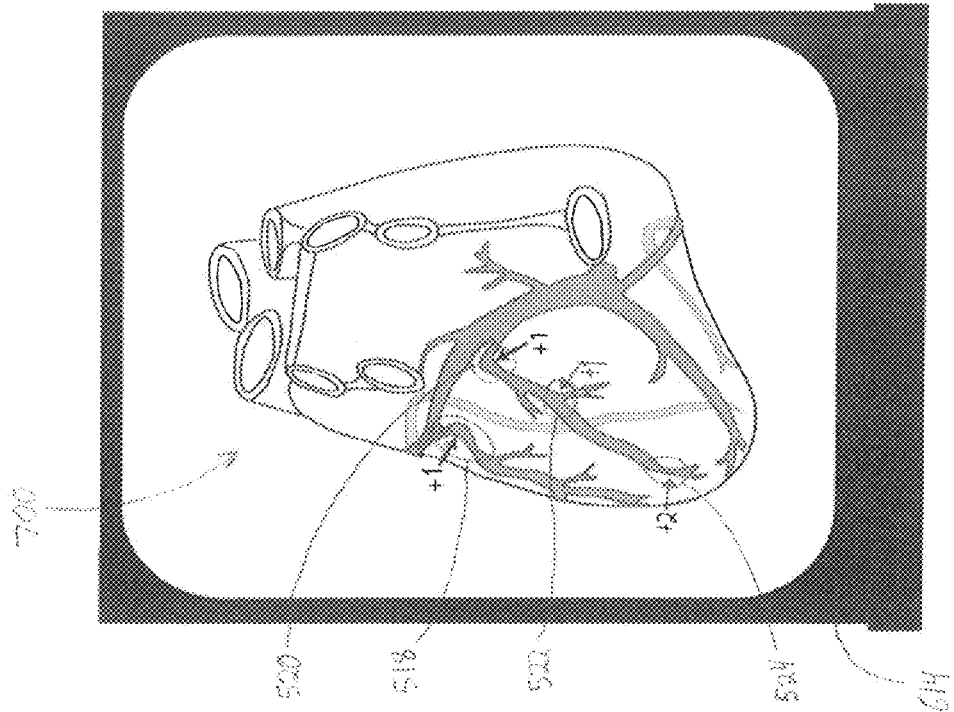

METHOD AND SYSTEM FOR CHARACTERIZING STIMULUS SITES AND PROVIDING IMPLANT GUIDANCE

BACKGROUND

One or more embodiments of the inventive subject matter relate to surgical planning for implant of a cardiac medical lead near a heart.

Heart failure is one of the most widespread and devastating cardiac afflictions, currently affecting approximately 6-10% of adults over the age of 65. One factor that contributes to heart failure is asynchronous activation of the ventricles such that the mechanical contraction is not coordinated effectively, thus compromising cardiac function. As a result, the pumping ability of the heart is diminished, and the patient experiences shortness of breath, fatigue, swelling, and other debilitating symptoms. The weakened heart is also susceptible to potentially lethal ventricular tachyarrhythmias.

One promising technique for reducing the risk of heart failure is cardiac resynchronization therapy (CRT), which seeks to normalize asynchronous cardiac electrical activation and the resultant asynchronous contractions. CRT delivers synchronized pacing stimulus to both ventricles using a pacemaker or an implantable cardioverter defibrillator (ICD) equipped with biventricular pacing capability. The synchronized pacing may be in the form of pacing pulses delivered from one or more electrodes on a cardiac medical lead to selected chambers of the heart. The stimulus is synchronized so as to help to improve overall cardiac function. CRT may have the additional beneficial effect of reducing the susceptibility to life-threatening tachyarrhthmias.

Cardiac resynchronization therapy (CRT) is achieved by positioning leads in traditional locations in the right chamber of the heart, and by maneuvering a left ventricular (LV) pacing lead through the coronary sinus and into the veins surrounding the left ventricle. Delivery of this LV lead is a challenging procedure that requires extensive fluoroscopy time for the patient and clinician. Venous anatomy in patients is highly variable. Some patients lack suitable veins for permanent placement of the lead or require the lead to be maneuvered through sharp angles.

Physicians may not readily recognize how challenging a particular patient's venous anatomy is until the procedure to implant a cardiac medical lead is underway. The physician will select an implant site and begin with his or her preferred implant tools and medical lead. The physician then escalates to more complex tools and/or different leads in the event an attempt fails to locate the lead at a desired implant site. The procedure, extended by the failed attempts, increases radiation exposure due to the extended fluoroscopy time, risks damage to the patient's veins, increases use of nephrotoxic contrast agents used in the fluoroscopy, leads to patient anxiety, and frustrates medical personnel. Eventually, the physician may ask for another physician to step in and take over, or may settle for a suboptimal, but easier to reach, location for the lead.

Accordingly, it would be beneficial to obtain pre-surgical and/or intraoperative knowledge of a patient's venous anatomy in and around the heart and to use that knowledge to provide guidance for physicians before and/or during the lead implantation procedure. Such surgical guidance may reduce or obviate the problems identified above that are associated with traditional lead implantation procedures.

SUMMARY

In an embodiment, a method is provided for characterizing an accessibility of potential stimulus sites in connection with surgical planning for implant of a cardiac medical lead near a heart of a patient is provided. The method includes obtaining image data representative of a coronary venous system for the heart of the patient to receive the lead. The method includes generating a venous map, based on the image data, representative of venous pathways for the heart of the patient. The method further includes analyzing the venous map to identify pathway features of interest (PFOI) within at least one select region of the venous pathways. The method also includes assigning scores to the PFOI based on at least one of predetermined feature-complexity relations or physician-entered complexity updates. Additionally, the method includes displaying treatment planning information to a user based on the scores.

In an embodiment, a procedure guidance (PG) system for characterizing an accessibility of potential stimulus sites in connection with surgical planning for implant of a cardiac medical lead near a heart of a patient is provided. The PG system includes an imaging device, a venous map circuit module, a pathway features of interest (PFOI) identification circuit module, a scoring circuit module, and a display device. The imaging device is configured to obtain image data representative of a coronary venous system for the heart of the patient to receive the lead. The venous map circuit module is configured to generate a venous map, based on the image data, representative of venous pathways for the heart of the patient. The PFOI identification circuit module is configured to analyze the venous map to identify PFOI within at least one select region of the venous pathways. The scoring circuit module is configured to assign scores to the PFOI based on at least one of predetermined feature-complexity relations or physician-entered complexity updates. The display device is configured to provide treatment planning information to a user based on the scores.

BRIEF DESCRIPTION OF THE DRAWINGS

FIG. 5 illustrates an exemplary venous map that may be characterized according to an embodiment.

FIG. 6 illustrates a table listing scores assigned to various pathway features of interest according to an embodiment.

FIG. 7 illustrates an exemplary venous map that may be characterized according to an embodiment.

DETAILED DESCRIPTION

Figure 1:
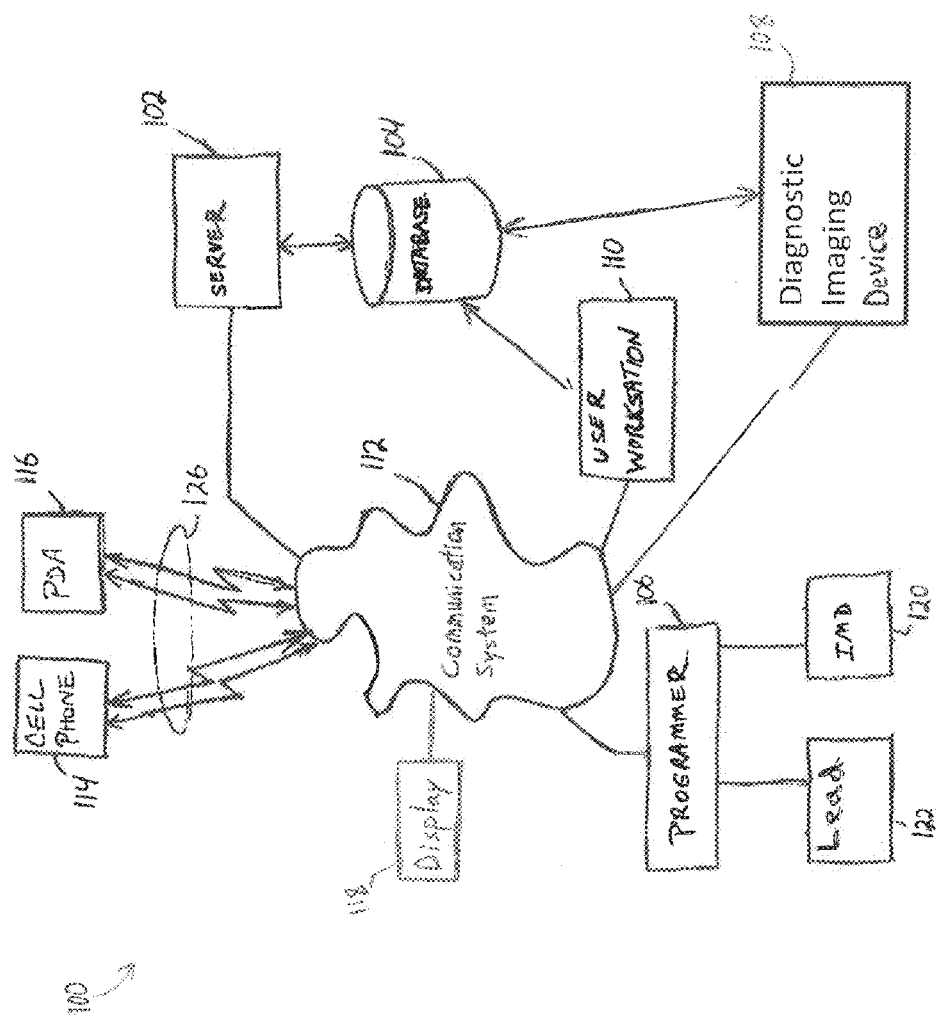
FIG. 1 illustrates a schematic diagram of a procedure guidance (PG) system that operates in accordance with one or more embodiments described herein.

The foregoing summary, as well as the following detailed description of certain embodiments, will be better understood when read in conjunction with the appended drawings.

As used herein, an element or step recited in the singular and proceeded with the word "a" or "an" should be understood as not excluding plural of said elements or steps, unless such exclusion is explicitly stated. Furthermore, references to "an embodiment" or "one embodiment" of the inventive subject matter are not intended to be interpreted as excluding the existence of additional embodiments that also incorporate the recited features. Moreover, unless explicitly stated to the contrary, embodiments "including," "comprising," or "having" (and various forms thereof) an element or a plurality of elements having a particular property may include additional such elements not having that property.

The block diagrams of embodiments herein illustrate various blocks labeled "module". It is to be understood that the modules represent circuit modules that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hard-wired to perform the functions described herein. Optionally, the hardware may include electronic circuits that include and/or are connected to one or more logic-based devices, such as microprocessors, processors, controllers, or the like. Optionally, the modules may represent processing circuitry such as one or more field programmable gate array (FPGA), application specific integrated circuit (ASIC), or microprocessor. The circuit modules in various embodiments may be configured to execute one or more algorithms to perform functions described herein. The one or more algorithms may include aspects of embodiments disclosed herein, whether or not expressly identified in a flowchart or a method.

To the extent that the figures illustrate diagrams of the functional blocks of various embodiments, the functional blocks are not necessarily indicative of the division between hardware and circuitry. Thus, for example, one or more of the functional blocks (e.g., processors or memories) may be implemented in a single piece of hardware (e.g., a general purpose signal processor, microcontroller, random access memory, hard disk, and/or the like). Similarly, the programs may be standalone programs, may be incorporated as subroutines in an operating system, may be functions in an installed imaging software package, and the like. Furthermore, to the extent that the figures illustrate flow diagrams of processes of various embodiments, the operations may be described by adding, rearranging, combining, or omitting the illustrated operations without departing from the scope of the processes as described herein. It should be understood that the various embodiments are not limited to the arrangements and instrumentality shown in the drawings.

The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. These devices may be off-the-shelf devices that perform the operations described herein from the instructions described above. Additionally or alternatively, one or more of these devices may be hard-wired with logic circuits to perform these operations.

FIG. 1 illustrates a schematic diagram of a procedure guidance (PG) system 100 that operates in accordance with one or more embodiments described herein. The PG system 100 may be configured to perform surgical planning for delivery of a cardiac medical lead into one or more coronary veins of the heart of a patient for cardiac resynchronization therapy (CRT). As used herein, surgical planning may include actions and/or steps performed pre-operatively and/or intraoperatively during the implantation procedure. The PG system 100 may be configured to leverage non-invasive imaging techniques to provide guidance for physicians prior to the medical lead implantation and positioning procedure. Optionally, the PG system 100 may leverage invasive and/or non-invasive imaging techniques to provide guidance during the procedure in addition to or as an alternative to pre-surgical imaging.

The PG system 100 includes a server 102 connected to a database 104, a programmer 106, diagnostic imaging equipment (e.g., one or more imaging devices and associated components) 108, a user workstation 110, and a display 118, all electrically connected to a communication system 112. Optionally, the PG system 100 may include other control, processing, and/or display devices, such as a cell phone 114 and/or a personal digital assistant (PDA) 116. Any of the processor-based components in FIG. 1 (e.g., workstation 110, cell phone 114, PDA 116, server 102, programmer 106) may perform the processes discussed herein.

The communication system 112 may be the Internet, a voice over IP (VoIP) gateway, a local plain old telephone service (POTS) such as a public switched telephone network (PSTN), a cellular phone based network, and the like. Alternatively, the communication system 112 may be a local area network (LAN), a campus area network (CAN), a metropolitan area network (MAN), or a wide area network (WAN). The communication system 112 serves to provide a network that facilitates the transfer/receipt of information such as cardiac image data and/or images, patient information, feature scoring information, surgical results and observations, and the like, as described below. The communication system 112 may be a wired network, a wireless network, or include both wired and wireless connectivity.

The server 102 is a computer system that provides services to other computing systems over a computer network. The server 102 may control the communication of and respond to requests for information such as images, data sets, scores, user-generated feedback, cardiac signal waveforms, and the other information described herein. The server 102 interfaces with the communication system 112 to transfer information between the programmer 106, the diagnostic imaging device 108, the display device 118, and the user workstation 110 to the database 104 for storage/retrieval of records of information. The server 102 may upload images and/or data sets from the diagnostic imaging equipment 108. Optionally, the server 102 may upload raw cardiac signals obtained from an implanted lead 122 or an implantable medical device (IMD) 120 via the programmer 106.

The database 104 stores information such as patient medical history, cardiac images and/or data sets, generated venous maps, feature scoring information, treatment planning information such as potential implant tools, potential medical leads to implant, and potential implant steps to follow during a medical lead implant procedure, a surgical planning database, and/or a physician-specific surgical history. The information is downloaded into the database 104 via the server 102 or, alternatively, the information is uploaded to the server from the database 104.

The programmer 106 may reside in a patient's home, a hospital, or a physician's office. The programmer 106 interfaces with the lead 122 and/or the IMD 120 that is and/or will be implanted into the patient during the medical lead implant procedure. The programmer 106 may control the stimulus therapy, such as timing, duration, and/or power of pacing pulses and/or shocks, that the medical lead 122 provides to the patient's heart. The programmer 106 may wirelessly communicate with the IMD 120 and utilize protocols, such as BLUETOOTH, GSM, infrared wireless LANs, HIPERLAN, 3G, satellite, as well as circuit and packet data protocols, and the like. Alternatively, a hard-wired connection may be used to connect the programmer 106 to the IMD 120. The programmer 106 is able to acquire cardiac signals from the surface of a person (e.g., ECGs), intra-cardiac electrogram (e.g., IEGM) signals from the IMD 120, and/or cardiac signal waveforms, ventricular and atrial heart rates, and detection thresholds from the IMD 120. The programmer 106 interfaces with the communication system 112, either via the internet or via POTS, to upload the information acquired from the lead 122 or the IMD 120 to the server 102.

The PG system 100 is used to plan for the implantation of a cardiac medical lead 122 of the implantable medical device (IMD) 120 in or near the heart of a patient. The IMD 120 may be a stimulation device, such as a pacemaker or an implantable cardioverter defibrillator (ICD), that provides pacing and or shocking pulses. The medical lead 122 has one or more electrodes that are used by the IMO 120 to deliver stimulation therapy to the heart in response to received signals. The lead 122 may be designed for implantation and/or placement in the "CS region," As used herein, the phrase "CS region" refers to the venous vasculature of the left ventricle, including any portion of the coronary sinus, great cardiac vein, anterior cardiac vein, left marginal vein, left posterior ventricular vein, middle cardiac vein, small cardiac vein, or any other cardiac vein accessible by the coronary sinus.

The lead 122 may include multiple electrodes at spaced apart locations along the lead 122. For example, the lead 122 may be a bipolar LV pacing lead or a Quartet™ LV pacing lead developed by St. Jude Medical Inc. (headquartered in St. Paul, Minn.), which includes four pacing electrodes on the lead—enabling up to 10 pacing vectors or configurations. The multipolar lead allows for the possibility of "electronic repositioning"—the ability to non-invasively change the site of LV pacing simply by programming pacing with a different electrode on the same multipolar lead. Optionally, the lead 122 may have more or less than four electrodes. For example, the bipolar LV lead may have two pacing electrodes.

The user workstation 110 may interface with the communication system 112 via the Internet, a LAN, or POTS, for example, to download cardiac images and/or image data, scoring information, general surgical planning information, physician-specific surgical history, patient medical history, or the like from the database 104 via the server 102. Alternatively, the user workstation 110 may download raw data from the diagnostic imaging device 108. Once the user workstation 110 has downloaded the cardiac images and/or image data, scoring information, surgical and medical histories, and surgical planning information, the user workstation 110 may process the information in accordance with one or more of the operations described above. The user workstation 110 may download the information and/or notifications to the display device 118 to be viewed by a physician, to the server 102 to be stored on the database 104, and/or to an external processing device such as the cell phone 114, the PDA 116, the programmer 106, or the like. For example, the user workstation 110 may communicate data to the cell phone 114 or PDA 116 via a wireless communication link 126. Optionally, the display device 118 may be integral to the user workstation 110 or the programmer 106. For example, the workstation 110 may be a laptop computer and the monitor of the computer may be used as the display device 118.

The diagnostic imaging device 108 interfaces with the communication system 112 to upload one or more of cardiac images and/or image data sets of a patient's heart to the server 102. The images and/or data sets may be obtained using magnetic resonance imaging (MRI), computed tomography (CT), ultrasound, fluoroscopy, single-photon emission computed tomography (SPECT), positron emission tomography (PET), or other cardiac imaging techniques known in the art. The cardiac images and/or data sets may be processed and displayed on the display device 118. In one or more embodiments, the cardiac images and/or data sets represent a patient's coronary veins in and/or around the heart prior to a medical lead implant procedure to obtain pre-surgical knowledge of the patient's anatomy. Optionally, at least some cardiac images and/or data sets may be captured during the medical lead implantation as well. For example, the clinician may use an intravascular ultrasound (IVUS) catheter which includes an ultrasound probe at a distal end of the catheter during the invasive procedure. The IVUS catheter may be used to record images and/or data sets of the venous pathways from within the blood vessels, and this information may be used to update and/or augment the images/data sets obtained prior to the surgery. The images and/or data sets may be reconstructed into 3D or 4D images of the patient's venous system before and/or after storage in the database 104.

It should be noted that FIG. 1 is schematic in nature and intended by way of example. In various embodiments, various aspects, functions, or structures may be omitted, modified, or added. Further, various devices, systems, functionality, or other aspects may be combined. For example, the programmer 106 optionally may include at least some of the structure (e.g., components, circuitry, etc.) and/or functionality described herein with respect to the display 118, database 104, and/or the user workstation 110. Optionally, the programmer 106, user workstation 110, database 104, and/or display 118 may be combined into a single device housing.

In one or more embodiments, the user workstation 110 is configured to analyze a patient's coronary veins in the cardiac images and/or image data set to score the relative difficulty of implanting the medical lead 122 along multiple potential lead routes. The lead routes extend from the coronary sinus through venous pathways, which are defined by coronary veins branching off of the coronary sinus. The venous pathways are scored to assess the difficulty of maneuvering the lead 122 through respective veins to potential stimulus sites. The stimulus sites are associated with the final location of one or more electrodes on the medical lead 122. The sites represent sensing and/or stimulus sites where an electrode located at a stimulus site may be used to sense and/or deliver stimulation in the form of pacing pulses or shocking pulses in CRT or defibrillation, respectively.

In one or more embodiments, the user workstation 110 is configured to analyze the images and/or image data set to identify geometric characteristics of the venous pathways on and about the heart. For example, geometric characteristics of the venous pathways including location, tortuosity, centroid path, bifurcation angle, and vessel width/diameter of the venous pathways are measured and/or calculated using image processing techniques. Identified features such as an acute angle, a U-turn, a rapid narrowing in a vein, and the like, increase the difficulty of maneuvering the lead 122 along a corresponding potential lead route to deliver an electrode to a potential stimulus site during the lead implant procedure.

The user workstation 110 may score the identified geometric obstacles in the venous pathways to reflect the relative difficulty of maneuvering the lead 110 past the respective features. This process may be fully or partially automated. For example, in a fully automated embodiment, the scores would be based on a mathematical representation of the venous pathways and/or some standard candidate regions of the venous system. In a partially automated embodiment, the user, such as a physician, may manipulate a user interface on the user workstation 110, cell phone 114, PDA 116, or the like, to select and/or zoom in on a particular area of a generated venous image (e.g., map) displayed on the display device 118. The user may select an area to query the workstation 110 to automatically score that particular area. The workstation 110 automatically scores particular geometric features by accessing scoring information from the database 104. The user may manually update automatically assigned scores and/or manually score a user-selected area based on the user's perception of the difficulty of traversing past the geometric obstacles in the area.

In an embodiment, the workstation 110 may compute a score for a potential stimulus site by aggregating the scores for all identified geometric obstacles along the lead route between the coronary sinus and the stimulus site. The workstation 110 may display the computed scores for multiple potential stimulus sites on the display device 118 on or next to an image of the patient's venous system to allow the user to compare the relative scores and locations of the potential stimulus sites. The relative scores may be graphically displayed as a color-coded heat map (e.g., red meaning more difficult to access, blue indicating less difficult to access), as integers associated with respective stimulus sites (e.g., higher number indicating higher difficulty), and/or the like. This information, including the calculated scores and displayed images, may be uploaded to the database 104 for storage.

The scores may be used to provide information to a physician used in planning before and/or during lead implant surgery. For example, the workstation 110 may be configured to suggest implant tools, a type of medical lead, and/or implant operations or steps likely to produce a successful surgical outcome, based at least partially on the scores. As used herein, steps may include one or more operations, methods, techniques, strategies, and/or the like that are performed by a clinician during, after, or in preparation for a cardiac lead implant procedure. A successful outcome may be characterized as a surgery having a low procedure time and no complications, thus minimizing failed implant attempts and limiting the patient's exposure to contrast agents and x-ray radiation. The suggestions and/or recommendations may be provided to the physician on the display device 118. The suggestions may be based on a standard database of surgical procedures and/or a record of the physician's own surgical history, either of which may be stored in the database 104 and accessible to the workstation 110. Optionally, during the procedure, a venous map including 3D reconstructed images generated from the images and/or image data sets captured by the imaging device 108 may be projected onto fluoroscopic images of the patient's heart and displayed on the display device 118 or another display device used during the procedure. Overlaying the venous map onto the fluoroscopic images may offer further guidance to the physician for implanting and steering the movements of the medical lead 122.

At the end of the procedure, the physician, a nurse, or a clinician may document information about the procedure, such as the final stimulus site, the final lead route, the tools and/or leads used, the operations, strategies, or steps employed during the procedure, and/or observations regarding the success of the tools used, leads used, and/or operations followed. The information may be input using a user interface on the user workstation 110, and the information may be documented in the database 104. In an embodiment, this documented information may update the standard database of surgical procedures and/or the physician-specific surgical history, such that the workstation 110 may consider this information when generating recommendations for future medical lead implant procedures. Thus, the treatment recommendations made by the user workstation 110 to a physician planning an implant procedure may be based at least in part on prior implant procedure results and observations by that physician or other physicians.

Figure 2:
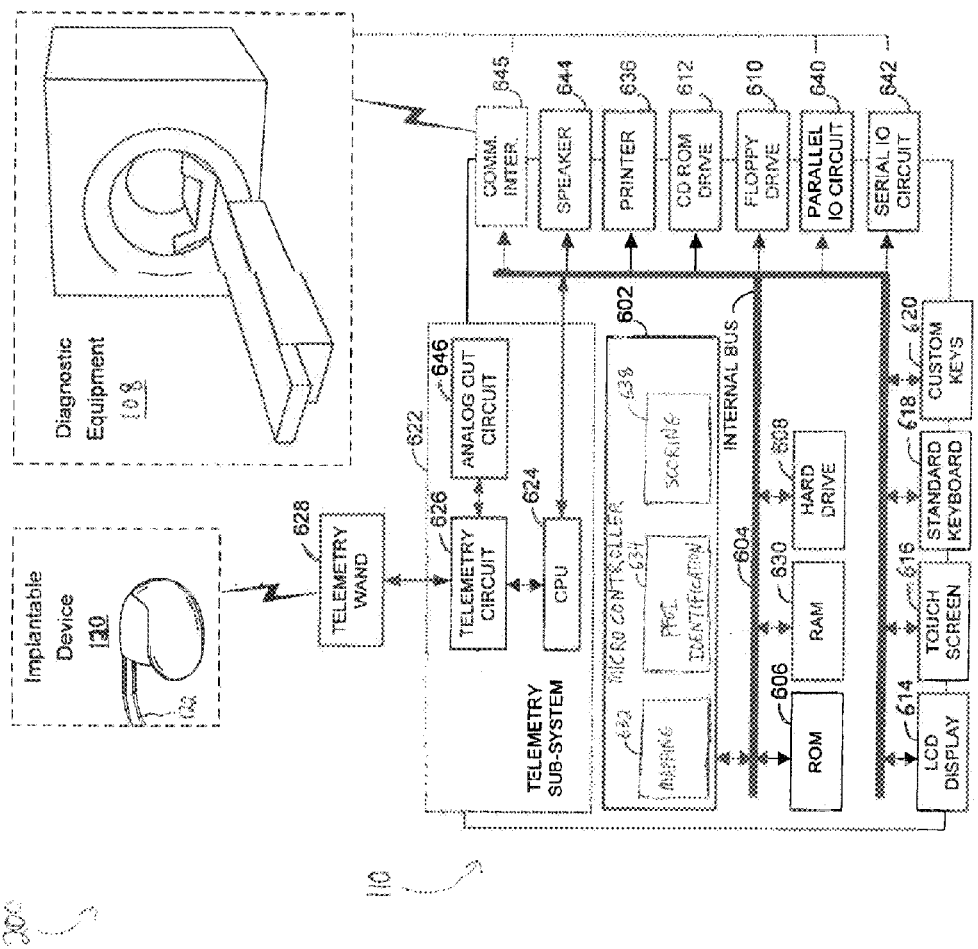
FIG. 2 illustrates a block diagram of a PG system that operates in accordance with one or more embodiments described herein.

FIG. 2 illustrates a block diagram of a procedure guidance (PG) system 200 that operates in accordance with one or more embodiments described herein. The PG system 200 is used to plan for the implantation of a cardiac medical lead 122 of an IMD 120 in or near the heart of a patient by leveraging non-invasive imaging techniques to provide guidance for physicians prior to and potentially during a lead implantation and positioning procedure. The PG system 200 may be the PG system 100 shown in FIG. 1. The PG system 200 includes at least one diagnostic imaging device 108, a user workstation 110 or another processing device, and a display 614. The display 614 may be the display device 118 shown in FIG. 1. The user workstation 110 may be a customized workstation, a desktop or portable computer, a tablet computer, a PDA, a cell phone, or the like. The user workstation 110 optionally may include the hardware and/or functionality of the workstation 110, programmer 106, server 102, and/or database 104 of the PG system 100 shown in FIG. 1.

The workstation 110 includes an internal bus 604 that couples/interfaces with a central processing unit (CPU) or microcontroller 602 (hereafter microcontroller), a read only memory (ROM) 606, a random access memory (RAM) 630, a hard drive 608, a communication interface 645, a speaker 644, a printer 636, a CD-ROM drive 612, a floppy drive 610, a parallel I/O circuit 640, a serial I/O circuit 642, a display device 614, a touch screen 616, a standard keyboard 618, custom keys 620, and/or a telemetry subsystem 622. The internal bus is an address/data bus that transfers information between the various components described herein. The workstation 110 may include or interface with other devices and/or components not shown in FIG. 2.

The display 614 is configured to display various forms of information related to the processes described herein to a user, such as a physician prior to or during a surgical procedure to implant a medical lead near a heart of a patient. The display 614 may be connected to a video display. The display 614 may be a monitor that is an integral component of the workstation 110 or an external device that is wirelessly connected or wired to the workstation 110. For example, the display device 614 may be an external tablet computer that communicates wirelessly to the workstation 110. The display 614 may be a liquid crystal display (LCD) light emitting diode (LED), plasma, cathode ray tube, or the like.

The touch screen 616 may display graphic user information relating to generated cardiac images and treatment planning information. The touch screen 616 accepts a user's touch input when selections are made. The keyboard 618 allows a user to enter data to displayed fields, as well as interface with the telemetry sub-system 622. Furthermore, custom keys 620 may turn on/off the PG system 200, such as in the case of emergencies. The printer 636 prints copies of images and/or reports for a physician to review or to be placed in a patient file. The speaker 644 provides audible tones to the user, such as a warning beep in the event improper input is provided by the physician. Optionally, the speaker 644 may provide treatment planning information audibly to the physician prior to and/or during a cardiac medical lead implant procedure. The floppy drive 610 accepts diskettes, and, optionally, the floppy drive 610 may include a USB port capable of communicating with a USB device such as a flash memory stick or an external hard drive. The CD-ROM drive 612 accepts CD ROMs and, optionally, may include a DVD port capable of reading and/or writing DVDs.

The user workstation 110 is operatively connected to diagnostic imaging equipment 108, which includes one or more imaging devices 108 such as an MRI unit, a CT unit, an ultrasound unit, a fluoroscopy unit, an echocardiogram unit, a positron emission tomography (PET) unit, and the like. As used herein, the diagnostic equipment 108 may be referred to as one or more imaging devices 108. In an embodiment, the imaging device 108 is configured to non-invasively obtain MRI and/or CT image data representative of a coronary venous system for the heart of a patient that is to receive the implantable cardiac medical lead 122. These imaging techniques are referred to herein as non-invasive because they do not require the use of an internal catheter to obtain the image data. Optionally, another imaging device 108, such as an invasive IVUS catheter, may be used during the lead implant procedure to capture ultrasound image data to update and/or augment the MRI and/or CT image data captured using the non-invasive imaging devices 108.

The images and/or image data may be obtained in two-dimensional (2D), three-dimensional (3D), and/or four-dimensional (4D) arrays (e.g., including time). For example, one or more of the imaging devices 108 may be a 4D CT unit, 4D MR unit, an electronic anatomical tracking system (e.g., such as MediGuide™ from St. Jude Medical Inc.), and/or an IVUS catheter with 4D capability. The 4D image data is configured to provide information about how the shape and dimensions of the coronary venous system change over time in response to the movement of the heart, such as during each cardiac cycle.

The imaging device 108 communicates with the workstation 110 via the communication interface 645, the parallel I/O circuit 640, and/or the serial I/O circuit 642. For example, the imaging device 108 may be wirelessly connected to or wired to a port of the communication interface 645, parallel I/O circuit 640, and/or serial I/O circuit 642, such that images and/or image data obtained by the imaging device 108 is transmitted to the workstation 110 through the communication interface 645 or the input circuits 640, 642. The communication interface 645 may be a network interface connected to a network (e.g., intranet, Internet, etc.). Optionally, other peripheral devices may be connected to the workstation 110 of the PG system 200 via the parallel circuit 640, the serial circuit 642, and/or the communication interface 645.

Optionally, the PG system 200 may include a telemetry sub-system 622 which provides components for directly interfacing with the implantable device/IMD 120. For example, the telemetry sub-system 622 may allow the PG system 200 to communicate with the IMD 120 to program or reprogram the IMO 120, even after implantation into the patient. As such, in addition to providing pre-implantation planning guidance and support during the implantation procedure itself, the PG system 200 may be configured to communicate with and control the IMD 120 post-implant. The telemetry subsystem 622 includes a central processing unit (CPU) 624 in electrical communication with a telemetry circuit 626, which communicates with both a telemetry wand 628 and an analog out circuit 646. The analog out circuit 646 includes communication circuits for controlling the transmission of analog output signals. The workstation 110 of the PG system 200 may wirelessly communicate with the implantable device 120 and utilize protocols, such as BLUETOOTH, GSM, infrared wireless LANs, HIPERLAN, 3G, 4G, satellite, as well as circuit and packet data protocols, and the like.

Alternatively, a hard-wired connection may be used to connect the workstation 110 to the IMD 120. Alternatively, another external device other than the workstation 110 may be used to program and/or adjust the programming of the IMD 120, such as the programmer 106 shown in FIG. 1.

The user workstation 110 of the PG system 200 includes a programmable microcontroller 602 that controls the operations of the workstation 110. The microcontroller 602 includes a microprocessor, or equivalent control circuitry, designed specifically to control interfacing with the imaging device 108 and perform the operations described herein. The microcontroller 602 may further include RAM or ROM memory, logic and timing circuitry, state machine circuitry, and I/O circuitry.

The microcontroller 602 includes the ability to process or monitor input signals (data) as controlled by a program code stored in memory. For example, the microcontroller 602 is configured to process and analyze images and/or image data sets received from the imaging device 108. Based on the processed images and/or data, the microcontroller 602 is configured to determine recommended treatment planning information regarding suggested lead implant tools, types of leads, and/or implant operations, such as one or more recommended lead routes for the cardiac medical lead 122 to be followed during the surgical lead implant procedure.

The details of the design of the microcontroller 602 are not critical to the present inventive subject matter. Rather, any suitable microcontroller 602 may be used. Among other things, the microcontroller 602 may receive, process, and manage storage of digitized cardiac data sets from the various imaging devices 108 and user input devices associated with the PG system 200. For example, the cardiac data sets may include cardiac image data, geometric feature identification data, geometric feature-complexity scoring data, user-entered complexity update data, treatment planning data, general and/or physician-specific prior procedure data, and the like. The cardiac data sets may be accessed by the microcontroller 602 from an internal memory of the workstation 110 or an external database, such as database 104 accessed via the server 102.

The microcontroller 602 includes a venous map circuit module 632, a pathway features of interest (PFOI) identification circuit module 634, and a scoring circuit module 638 (among other things). The venous map circuit module 632 is configured to generate a venous map (e.g., a map showing the coronary veins) based on the images and/or data set received from the memory or from the imaging device 108. The venous map may represent mapping information designating boundaries or walls and intersection nodes of the veins in the venous system (e.g., great, middle, and small cardiac veins). The mapping boundaries and nodes may be defined relative to the same coordinate system and reference point as the images or imaging data set. Optionally, the venous map may represent information denoting segments, intersection nodes, branches, segment directions, segment thicknesses, and the like. As described below, the venous map circuit module 632 may form the venous map by performing automated segmentation analysis of the image data, such as region growing of areas within the venous system. Optionally, other analysis techniques may be used to identify and map the venous system using the data set or images. The venous map may be displayed on the display 614 for viewing by a user.

The PFOI identification circuit module 634 is configured to analyze the venous map to identify pathway features of interest (PFOI) within at least one select region of the venous pathways. As described below, the PFOI circuit module 634 may use image processing to provide mathematical representations of the geometry of the venous map. For example, the PFOI circuit module 634 may calculate characteristics of the venous pathways such as location, centroid path, width, length, bifurcation angles, and the like. The characteristics are used in characterizing the accessibility of various potential stimulus sites. For example, it may be difficult to access a certain stimulus site if the venous pathway between that stimulus site and an upstream origination site at the coronary sinus includes a significant narrowing in the vessel width, includes a U-turn out of a bifurcation, and/or is significantly tortuous. As used herein, upstream and downstream refer to the movement of the lead during implantation (e.g., not the flow of blood through the coronary veins), so the "stream" flows in the direction from the coronary sinus towards the potential stimulus sites within tributary coronary veins.

The PFOI identification circuit module 634 may be configured to recognize certain vein characteristics and autonomously identify the corresponding locations in the venous pathways as PFOI. The identified PFOI overlaid on the venous map may be displayed on the display 614 for viewing by the physician. In an alternative to automatic identification of the PFOI, the PFOI circuit module 634 may be configured to respond to user inputs, such as the physician using the touch screen 616 or another user interface to identify user-selected PFOI. In response, the PFOI circuit module 634 calculates the vein characteristics within and/or upstream of the areas identified by the user.

The scoring circuit module 638 is configured to assign scores to the PFOI based on at least one of predetermined feature-complexity relations or physician-entered complexity updates. For example, the scores may be associated with the geometric characteristics of the features, such that a PFOI that includes a geometric obstacle that would be more difficult to traverse than another PFOI may be assigned a higher score, as described further below. The predetermined feature-complexity relations and/or physician-entered complexity updates used to assign the scores and/or the resulting assigned scores may be stored in a database in the PG system 200, such as in the hard drive 608 of the workstation 110 or a database external to the workstation 110 (e.g., database 104 shown in FIG. 1). Alternatively or optionally, a user such as a physician may set the score for specific PFOIs based on his or her own experiences. For example, the physician may set the score for one or more PFOI instead of the scoring circuit module 638 autonomously assigning a score, or the physician may override the score assigned by the scoring circuit module 638 with a physician-selected score.

To assess the overall difficulty of implantation at a potential stimulus site, the scoring circuit module 638 may combine or tabulate the scores associated with the PFOI through the potential lead route from the upstream origination site at the coronary sinus to a potential stimulus site to generate a total value (e.g., an aggregated score) associated with the potential stimulus site. By comparing total values for various potential stimulus sites, the scoring circuit module 638 may make a recommendation to the physician of one or more potential stimulus sites that have the greatest probability of a successful implant surgery based on the venous geometry. For example, a potential stimulus site that is determined to be less difficult to access (e.g., based on the aggregated scores) may have a greater probability of successful implantation. One or more of the calculated total values may be displayed on the display device 614 for the physician to view.

In addition to assigning scores to the PFOI and aggregating the scores to determine the total values, the scoring circuit module 638 may retrieve treatment planning information for display on the display device 614. The treatment planning information may include the recommended potential stimulus site or sites, as stated above, and may also identify a suggested final lead route through the venous pathways to locate one or more electrodes at the suggested stimulus sites. The treatment planning information may include additional information, such as recommended implant tools, types of leads, and/or steps to follow during implantation of the medical lead. Optionally, the treatment planning information may be communicated to the user audibly using the speaker 644 instead of or in addition to displaying the information on the display device 614.

Figure 3:
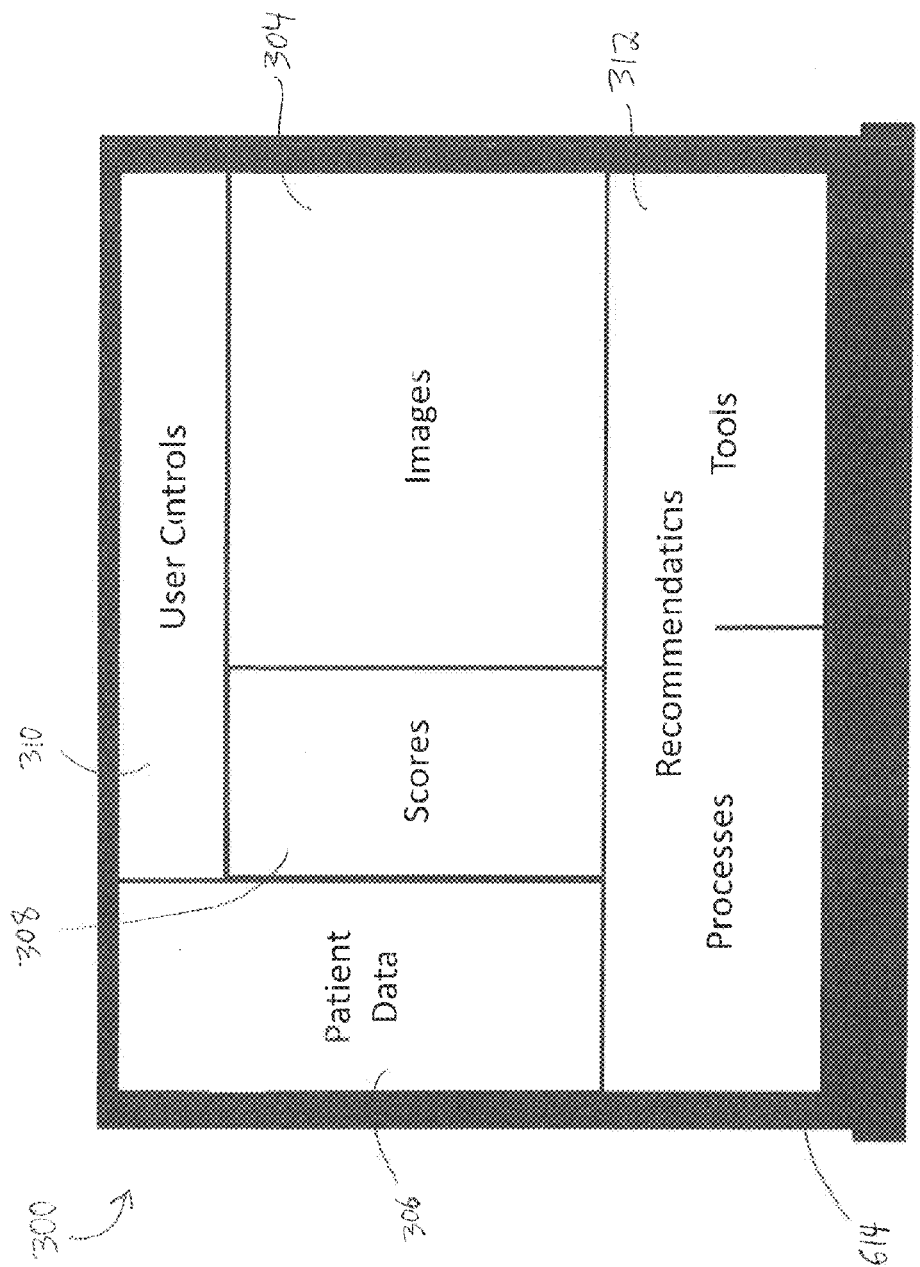
FIG. 3 illustrates a graphical display for a PG system according to an embodiment.

FIG. 3 illustrates a graphical display 300 for the PG system 200 according to an embodiment. The graphical display 300 is displayed on the display 614, which may be the display device 118 of FIG. 1. The graphical display 300 may represent a display that is presented to a user (e.g., physician) when using the PG system 200 to plan for a medical lead implantation procedure. The display 300 may be manipulated by a user using a graphical user interface, such as a touch screen, a keyboard, a mouse, and the like. In an embodiment, the screen area may be segmented into defined areas that provide specific types of information to the user. For example, image area 304 may provide images and/or video of a patient's heart and venous system. The images may be a generated venous map, and optionally may be a venous map with scores overlaid on a three-dimensional anatomical image of the heart. For example, the venous map may be an anatomical image of the venous system with scores designated directly (e.g., superimposed) on the anatomical image of the venous system. The scores may be numeric, color coded (e.g., as in a continuous heat map), or otherwise designated graphically and associated with corresponding potential stimulus sites to comparatively represent projected accessibilities of the potential stimulus sites. Patient data area 306 may provide data/information regarding the patient who will be receiving the implantable lead and whose cardiac venous system is represented in the images in area 304. The patient information may include identification information (e.g., name, birth date, etc.), patient medical history, other patient-specific measured cardiac data (e.g., heart rate, intracardiac electrograms (IEGMs), etc.), and the like.

Score area 308 of the graphical display 300 may provide various scores for identified geometric features of interest in the venous pathways of the venous system map displayed in image area 304. For example, after the workstation 110 scores the identified pathway features of interest (PFOI), the scores and associated PFOI may be listed in area 308. Alternatively, lead lines may extend from each of the scores in area 308 directly to respective PFOI indicated on the venous map shown in area 304. Area 310 may include various user controls that allow the user to navigate and/or customize the graphical display 300. For example, the user controls may include image manipulation tools, such as zoom and rotate, to alter how the 3D venous map is displayed, save and upload tools, tools that command the workstation 110 to generate scores and/or recommendations, user preferences tools, tools that allow the user to manipulate auto-generated scores and/or recommendations, and the like.

Recommendation area 312 of the graphical display 300 may be designated to provide suggestions and/or recommendations to a physician regarding the lead implant procedure. The recommendation area 312 may be sub-divided to display recommendations regarding which implant tools and/or medical leads to use and which processes or steps to follow in order for the procedure to have the calculated greatest probability of success. The recommended processes may include suggested lead routes and potential stimulus sites (e.g., based on low calculated difficulty scores), implantation sites, lead-maneuvering strategies, and the like. The recommended tools may include suggested catheters and/or guidewires. The recommended types of medical leads may be selected based on characteristics, such as amount of electrodes (e.g., unipolar, bipolar, quadripolar, or the like), length, diameter, materials, shape, or the like. Optionally, multiple recommendations may be provided, and the recommendations may be ranked, for example, as first, second, and third best options. Optionally, the recommendations may be based on the venous system overall, or may be specific to selected regions, stimulus sites, or venous pathways of the venous system. For example, the graphical display 300 may display recommendations specific to a potential stimulus site located in the great cardiac vein in response to the user selecting the stimulus site.

It should be noted that the graphical display 300 of FIG. 3 is intended by way of example and is schematic in nature. In various embodiments, various areas and/or boundaries between the areas 304-312 may be added, omitted, or arranged differently. Various areas 304-312 may be separated into other sub-areas and/or be shared with other areas. For example, the scores optionally may be displayed in the same area of the display 300 as the cardiac images in addition to or instead of having a separately defined score area 308.

Figure 4:
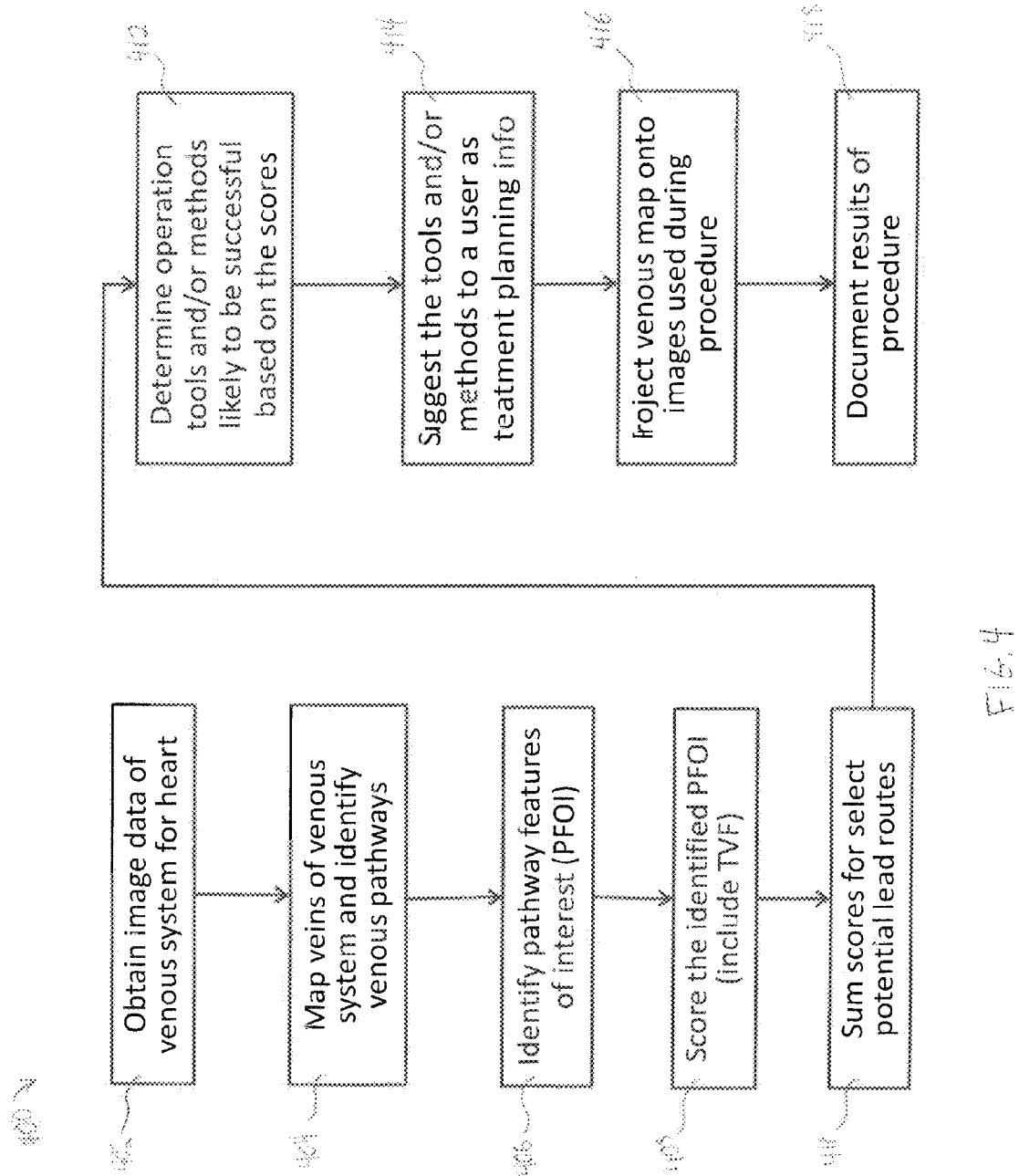
FIG. 4 illustrates a flow chart for a process for characterizing accessibility of potential stimulus sites in connection with surgical planning for implant of a cardiac medical lead near or on a heart of a patient according to an embodiment.

FIG. 4 illustrates a flow chart for a process 400 for characterizing accessibility of potential stimulus sites in connection with surgical planning for implant of a cardiac medical lead near or on a heart of a patient according to an embodiment. The process 400, for example, may employ structures or aspects of various embodiments (e.g., systems and/or methods) discussed herein. For example, the process 400 may be performed using the PG system 200 shown in FIG. 2. The process 400 is described herein with reference to the user workstation 110, the display 614, and the imaging device 108 shown in FIG. 2, although other devices may be used instead of or in addition to these devices. In various embodiments, certain aspects of the process 400 may be omitted or added, certain aspects may be combined, certain aspects may be performed simultaneously, certain aspects may be performed concurrently, certain aspects may be split into multiple aspects, certain aspects may be performed in a different order, or certain aspects or series of aspects may be re-performed in an iterative fashion.

In various embodiments, some portions, aspects, and/or variations of the process 400 may be able to represent one or more algorithms to direct hardware to perform operations described herein. For example, the process 400 may be implemented in an algorithm that controls the workstation 110 of the PG system 200 to automatically process and analyze the received images and/or image data set to provide guidance to a physician prior to and/or during a cardiac medical lead implant procedure according to the operations described herein. The process 400 may be fully automated or partially automated.

At 402, an image data set of a venous system for a heart of a patient is obtained. The image data may include data for the entire heart with the venous system thereon. Alternatively, the image data may include data only for the venous system on and about the heart. The heart and/or venous system of the patient may be imaged prior to the patient undergoing the surgical procedure to implant a cardiac medical lead and/or during the procedure. The image data set may be generated from a diagnostic scan of the patient at an earlier examination or immediately prior to the surgical procedure. The image data set is obtained using diagnostic imaging techniques that may include MRI, CT, echocardiogram, positron emission tomography (PET), ultrasound, fluoroscopy, and the like. In an embodiment, an MRI or CT imaging device collects MRI or CT image data, respectively. Optionally the image data set The image data set may represent the raw image data set generated by the diagnostic imaging equipment and/or one or more images that are rendered or otherwise generated from processing the raw image data set. The imaging device or equipment may obtain a set of images and/or image data of the heart from different projections. The images and/or image data may be reconstructed to form 3D images of the patients coronary veins and venous system. The term "venous system" as used herein refers to the system of coronary veins in and along the heart, including the coronary sinus, great cardiac vein, middle cardiac vein, and other veins that carry deoxygenated blood from the heart muscle to the right atrium. Optionally, the image data set may be a dynamic 4D data set that records time as well as spatial parameters. The 4D data set may be reconstructed to form time-varying 3D images or video of the venous system.

At 404, the veins of the venous system in the image data set are analyzed and mapped to generate a venous map. In an embodiment, the veins are mapped by an automated segmentation technique or analysis of the image data, such as threshold-based 3D region growing. For example, the automated segmentation technique may be performed to highlight the coronary veins. The venous map may be generated by the venous map circuit module 632 of the workstation 110 shown in FIG. 2 after receiving image data collected from the imaging device 108. The venous map may be generated by reconstructing multiple 2D images into a 3D image. In an embodiment, the venous map may be dynamic such that it varies over a recorded time period.

At 404, venous pathways are identified in the venous map. The venous map may be representative of the venous pathways for the heart of the patient that is to receive the lead. For example, since the medical lead may be delivered along the left ventricle through the coronary sinus and tributary coronary veins, the coronary veins define the venous pathways that the lead is transported through. The lead is maneuvered along a course or route through the venous pathways to place the one or more electrodes at the selected stimulus site or sites. The venous pathways may be identified during the segmentation technique or another type of image processing technique.

At 406, pathway features of interest (PFOI) are identified within at least one select region of the venous pathways of the venous map. The select region(s) may be the individual coronary veins that are represented by respective venous pathways, pre-defined epicardial regions of the heart, and/or user-selected areas of the venous system. In an embodiment, image processing techniques are applied to the venous pathways to identify characteristics that mathematically describe the geometry of the venous system. For example, characteristics of the venous pathways, such as centroid path, vessel width, location of branch bifurcations, angles of coronary veins extending from bifurcations, tortuosity of segments of the venous pathways, and the like, may be calculated using image processing techniques that are known in the art. The image processing and calculations may be performed by the PFOI identification circuit module 634 of the user workstation 110 shown in FIG. 2 by analyzing the venous map. The characteristics describing the geometry are analyzed to identify features, or PFOI, that reflect the difficulty or ease of implantation. The characteristics are used to score the identified PFOIs based on the relative difficulty of traversing the lead through the respective geometric features.

Referring now to FIG. 5, FIG. 5 illustrates a venous map 500 that may be displayed according to an embodiment. The venous map 500 illustrates a patient's heart 502 and venous system 508, including the coronary sinus 504 and coronary veins 506 that extend from the coronary sinus 504. The venous map 500 may be displayed on the display 614 shown in FIG. 2 to be viewable to a user (e.g., physician). The venous system 508 may be displayed in one or more different colors than the heart 502 based on the results of the automated segmentation technique performed when generating the venous map 500. Each of the coronary veins 506 represents a potential venous pathway through which the medical lead (e.g., lead 122 shown in FIG. 2) may be routed to locate one or more electrodes at selected stimulus site(s). For example, the selected stimulus site(s) may be one of multiple potential stimulus sites located within a first venous pathway 512, a second venous pathway 514, and/or a third venous pathway 516, as shown in FIG. 5.

By using image processing, the PG system 200 may autonomously identify PFOI 510 within the venous pathways 512-516 that may pose as obstacles during lead implantation. Optionally, one or more PFOI 510 may be identified manually by a user manipulating a user interface (e.g., touch screen, keyboard, mouse, etc.) to select one or more user-identified PFOI on the displayed venous map 500. In an embodiment, the workstation 110 may automatically identify multiple PFOI using image analysis, but a user (e.g., a physician) may manually identify additional PFOI or may manually edit the automated analysis, such as to remove a PFOI that the physician deems is not an obstacle worth noting and scoring. Thus, a user may manually override and update the automated processes performed by the PG system 200.

The PFOI 510 may be one or more pre-determined geometric shapes, such as an acute angle, a U-turn change of direction in a pathway, a branch bifurcation, pathway narrowing of the vessel width or diameter within a certain distance (e.g., 5 mm), a small diameter relative the lead (or introducer), overall tortuosity of a segment of a venous pathway, and the like. These geometric shapes may be known obstacles that are difficult to maneuver a lead therethrough. The geometric shapes to search for may be stored in a database that is accessible to the user workstation 110 shown in FIG. 2. For example, the geometric shapes may be stored in the internal memory of the workstation 110, such as the hard drive 608, and/or may be stored in a database, such as database 104, external to the workstation 110. The stored information may also include equations and/or parameters used to characterize and identify the pre-determined geometric shapes in the images and/or image data.

For example, an angle in any anatomical plane (sagittal, coronal, or frontal) between 1 and 90 degrees, optionally between 20 and 80 degrees, may be identified as an acute angle. In another example, a U-turn may be characterized mathematically according to the equation $t_i * t_{i-1} < -0.707$, where $t_{i-1}$ represents a unit vector tangential to an upstream section of the venous pathway upstream of or prior to the turn (e.g., between the turn and the coronary sinus), and $t_i$ represents a unit vector tangential to a downstream section of the venous pathway after the turn.

A narrowing region may be identified when, for example, the width of the venous pathway decreases by over 25% along a segment of the venous pathway. The narrowing region may be calculated mathematically according to the equation $100 * (w_{i-1} - w_i)/w_{i-1} \geq 25\%$, where $w_{i-1}$ represents the width of an upstream first section of the coronary vein, and $w_i$ represents the width of the coronary vein at a second section downstream of the first section (e.g., closer in proximity to a potential downstream stimulus site). The tortuosity of a segment of a venous pathway may be calculated according to the equation $\tau = L_{Vein}/L_{Direct}$, where $L_{Vein}$ is the distance along the vein path from a defined upstream location to a defined downstream location, and $L_{Direct}$ is the distance of a straight line from the defined upstream location to the defined downstream location. For example, to calculate the overall tortuosity of a venous pathway, the upstream location may be the coronary sinus and the downstream location may be the potential stimulus site. The tortuosity of at least a segment of a venous pathway may be flagged as a PFOI if the value of $\tau$ exceeds a designated threshold, such as 2. Furthermore, a bifurcation may be identified as a split or fork in a venous pathway, and the bifurcations may be detected during the automated segmentation operation.

As shown in FIG. 5, for example, a first feature 518 may be identified as a tortuous segment of the venous pathway 512, a second feature 520 may be identified as an acute angle within the venous pathway 514, a third feature 522 may be identified as a bifurcation within the venous pathway 514, and a fourth feature 524 may be identified as a narrowing of the venous pathway 514. The identified features 518-524 shown in FIG. 5 are merely exemplary and do not constitute the only features of the venous pathways that may be characterized as PFOI.

Referring back to FIG. 4, at 408, the identified PFOI are scored. In an embodiment, scores may be assigned to the individual PFOI based on predetermined feature-complexity relations and/or physician-entered complexity updates. Thus, the score assigned to a PFOI corresponds to the complexity or difficulty to traverse the PFOI with a medical lead during implantation. For example, a feature that is a greater obstacle may be assigned a higher score. In an embodiment, the assigned scores may be points, such as +1, +2, and +3. Alternatively, or in addition, the scores may be shown using colors or other indicators. For example, more difficult PFOI may be displayed as a darker color of the venous pathway around the respective PFOI or by an inserted "x" or frowning emoticon, for example, on or next to the PFOI. The scoring may be fully and/or partially automated. In automated scoring, the scores may be based on predetermined feature-complexity relations stored in a database on the PG system 200, such as the hard drive 608 of the workstation 110 shown in FIG. 2 or the database 104 shown in FIG. 1. The scoring circuit module 638 of the workstation 110 may retrieve a score for a respective feature from the database based on the classification of the PFOI (e.g., whether the feature is a narrowing or a U-turn) and/or other characteristics (e.g., an acute angle of 20 degrees optionally may be scored higher than an acute angle of 70 degrees).

FIG. 6 illustrates a table 600 listing scores assigned to various PFOI according to an embodiment. The table 600 includes multiple predetermined feature-complexity relations. Optionally, the table 600 may be stored in a database 104 (shown in FIG. 1) and/or at the workstation 110 (shown in FIGS. 1 and 2) and accessed by the scoring circuit module 638 (shown in FIG. 2) of the workstation 110 to assign scores to identified PFOI. For example, once a given PFOI is identified as a narrowing, for example, because the mathematical properties of the region indicate that the width of the venous pathway narrows by over 25% within the region, the scoring circuit module 638 may access the table 600 from the database. As shown in table 400, a narrowing of the coronary vein by at least 25% is assigned 2 points. Thus, the scoring circuit module 638 may assign that given PFOI as 2 points.

Other feature-complexity relations shown in table 600 are that a bifurcation is assigned 1 point, an acute angle is assigned 1 point, a U-turn is assigned 3 points, and a tortuous region is assigned $r*C$ points, where C is a constant multiplier. For example, C may be 0.5, 1, 1.5, and the like. Thus, if the τ is calculated to be 2.5, and C is 0.5, the tortuous region may be assigned 1.25 points. The values shown in table 600 indicate that a narrowing is a greater obstruction to a potential lead route than a bifurcation, but not as great of an obstruction as a U-turn. Optionally, table 600 may be physician-specific, such that the point values and geometric features in the feature-complexity relations are tailored to the skills and difficulties of the physician as opposed to physicians in general. The table 600 optionally may be displayed on the display 614 to a user, such as to allow a physician to update the features and/or points in the feature-complexity relations. It is noted that the predetermined assigned point values shown in table 600 are merely examples, and do not represent all possible features that may be assigned points. The point values in other embodiments may vary from the values shown in table 600, both in terms of magnitude and relation to the point values of other PFOI. For example, an acute angle in another embodiment may be assigned 3 points, and a U-turn may be assigned 2 points.

FIG. 7 illustrates a venous map 700 according to an embodiment. The venous map 700 may be the venous map 500 shown in FIG. 5. The venous map 700 is displayed on the display 614. Although shown in two dimensions, the venous map 700 may be displayed as a 3D image. In FIG. 7, the identified PFOI 518, 520, 522, and 524 have been scored. The score may represent indicia indicative of a difficulty level within a range of difficulties between least and most difficult lead placement. Optionally, the scores may be displayed on the venous map 700 to correspond with the respective PFOI of the venous pathways, as shown in FIG. 7. The scores may be displayed as numerals over a range from least difficult to most difficult, as color codes over a range, and the like. Optionally, a key may be displayed indicating the range and color codes associated with each difficulty level. The PFOI 518-524 have been scored according to the feature-complexity relations shown in table 600 of FIG. 6. For example, PFOI 520 is an acute angle, and it is assigned +1 point, while PFOI 524 is a narrow region, so it is assigned +2 points, PFOI 518 is a tortuous region which may be assigned +1 point if, for example, τ was calculated as 2 and C is set at 0.5. PFOI 522 is a bifurcation, which is assigned +1 point.

During normal operation of the heart, the orientation and/or dimensions of some of the venous pathways may not be entirely static. For example, some coronary veins may expand or contract during the cardiac cycle in response to pressure and/or blood flow, affecting the diameter of the venous pathways. In addition, as the chambers of the heart contract and relax, the acuteness of angles and the tortuosity of the veins may vary. Thus, for example, although a certain PFOI may be assigned a "+1" (e.g., little difficulty) based on an image captured at a given moment, the same PFOI may actually be much more difficult at other times in the cardiac cycle, such that the PFOI would be assigned a higher score (e.g., +3, +4, etc.) based on images captured at those other times. In an embodiment using 4D image data sets, the scoring circuit module 638 of the PG system 200 may account for these changes based on time, or temporal variant features (TVF), of the PFOI. For example, the scoring circuit module 638 may score the identified PFOI at multiple times in order to calculate a TVF (e.g., a parameter that accounts for changes over time). Thus, if the PFOI in the example above was scored as a +1 based on the static image analyzed, but that PFOI is often scored as a +3 at other times in the TVF may raise the score to at least +2 or even +3. Factoring in TVFs while scoring the PFOI may more accurately represent the difficulty of accessing a potential stimulus site through the PFOI.

In an embodiment in which a user selects one or more user-selected PFOI, the scoring circuit module 638 of the workstation 110 (shown in FIG. 2) may be configured to automatically score the used PFOI by calculating the degree of an angle or turn within the area selected using image processing, and adding an appropriate number of points. The number of points may be determined using feature-complexity relations, as described above.

As with identifying PFOI, scoring the PFOI may optionally be only partially automated to allow a user to set scores at new venous locations or update scores that were already automatically assigned. These user-selected scores are referred to herein as physician-entered complexity updates. For example, a physician at a user interface may select one or more PFOI, and add or subtract the points assigned to those PFOI. The physician may find one type of PFOI particularly problematic, and so may add a point or two. The physician may find another type of PFOI relatively easy to navigate a lead through, and so may subtract a point or even delete the PFOI entirely. Optionally, points may be added by the physician using the touch screen 616 of the workstation 110 or a mouse to click on the places that he anticipates to be particularly difficult, and the algorithm may add up the clicks to convert to a point value. Alternatively or additionally, the physician may highlight a select location and type in a desired point value using the touch screen 616 or the keyboard 618.

Thus, the physician may customize the scoring to the physician's particular skills and preferences. In an embodiment, the workstation 110 may store the physician-entered complexity updates in a database and use the updates to update the predetermined feature complexity relations. As such, when planning for a future implant procedure, the system may score identified PFOI according to the updated predetermined feature-complexity relations (e.g., that include the prior physician-entered complexity updates), so the PG system 200 may be configured to adapt over time to the preferences of specific physicians.

Referring back to FIG. 4, at 410, scores for select potential routes through the venous pathways are summed. The scores along each of multiple potential routes are totaled to provide a total value which represents a difficulty score of locating an electrode of the implanted medical lead at a potential stimulus site within the respective venous pathways. For example, for a selected potential stimulus site along a given venous pathway, all of the scored PFOI along the venous pathway between the stimulus site and the coronary sinus are aggregated. The total value represents risk weights associated with approaching the corresponding potential stimulus sites with the medical lead, since the lead will have to be maneuvered through each of the PFOI whose scored were accumulated in order to place an electrode at the selected stimulus site. In an embodiment, the scoring circuit module 638 aggregates the scores along respective venous pathways. The scores may be aggregated to show total values (e.g., total or aggregated scores) for auto-selected and/or user-selected potential stimulus sites. The display device 614 may display the aggregated scores associated with one or more of the potential stimulus sites on the venous map for the physician to view. Optionally, the scores may be aggregated to compute a total value for each coronary vein by adding the scores along each respective venous pathway, or total values may be computed based on regions of the venous map. For example, the regions that are scored may be predefined epicardial regions of the heart. When dynamic 4G image data sets are used to generate the venous map, the user may have an option whether or not the scores are aggregated using TVF-adjusted PFOI scores.

Figure 8:
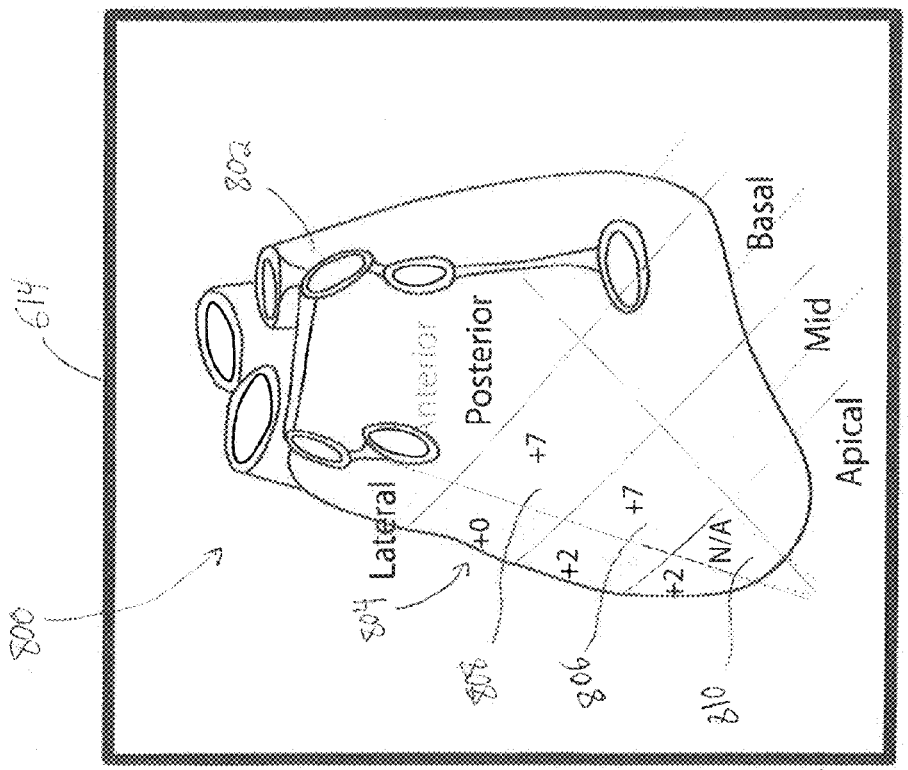
FIG. 8 illustrates an exemplary venous map of a heart that is allocated into multiple scored epicardial regions according to an embodiment.

FIG. 8 illustrates a venous map 800 of a heart 802 that is allocated into multiple scored epicardial regions 804. The venous map 800 may be the venous map 500 shown in FIG. 5, although the venous system 508 optionally may not be displayed on venous map 800. The venous map 800 is displayed on the display 614. The map 800 may be viewed by a user and manipulated by the user using a user interface on or coupled to the user workstation 110 (shown in FIG. 2). The map 800 may be divided into posterior, lateral, and anterior columns, and into apical, mid, and basal rows. One example region is a mid-posterior region 806. The regions 804 may be predefined, such that the dividing lines are overlaid onto the venous map 800 automatically. In an embodiment, the total values (e.g., aggregated scores) may be tabulated according to the epicardial regions 804. For example, the scoring circuit module 638 of the workstation 110 may aggregate the scores assigned to individual PFOI within and/or upstream of each region 804.

Each region 804 is assigned a total value, which gives the physician the opportunity to weigh the risk of approaching each region. For example, the mid posterior region 806 may have a total value of +7 points. Thus, the PFOI within the region 806 and/or upstream of region 806 in a basal posterior region 808 may have a combined score of +7 points. The PFOI within the basal posterior 808 region may be included in the score for the mid posterior region 806 because, to locate an electrode in the mid posterior region 806, the lead would have to be maneuvered from the coronary sinus through the basal posterior region 808 (e.g., and all PFOI therein) to reach the mid posterior region 806. In an embodiment, the scored regions 804 may be displayed to a user on the display 614 with the scores for each region 804 labeled, as shown in FIG. 8. Optionally, in a region 804 where no coronary veins are present, such as the apical posterior region 810, the region 804 may be not scored and/or may be labeled as "N/A" to inform the user that there are no potential stimulus sites within the region 804.

Figure 9:
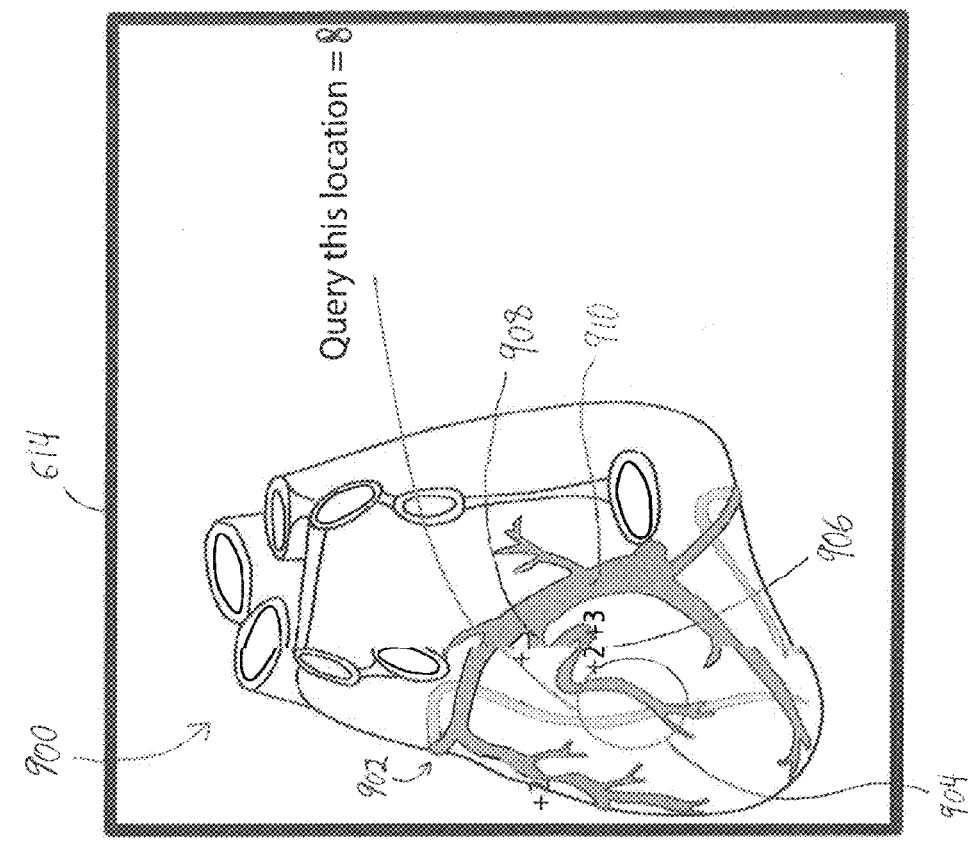
FIG. 9 illustrates an exemplary venous map that may be characterized according to an embodiment.

FIG. 9 illustrates a venous map 900 according to an embodiment. The venous map 900 may be similar to the venous map 500 shown in FIG. 5, although the venous system 902 (e.g., structure of the coronary veins) shown in map 900 may be different than the venous system 508 displayed on map 500. The venous map 900 may be displayed on the display 614 of the workstation 110 to be viewable to the user (e.g., physician). In an embodiment, the scores for select potential lead routes are summed based on user-selected sites or areas of the venous map 900. For example, the PG system 200 (shown in FIG. 1) may be configured to allow a physician to query one or more particular locations of the map 900. The physician may zoom in on or select a particular area, which would represent a potential stimulus site, and all upstream scored points (e.g., from the selected area to the coronary sinus) would be summed to give an aggregated score or total value for this potential stimulus site.

For example, using the touch screen 616 and/or another user interface of the workstation 110, the physician may designate a first location 904. The scoring circuit module 638 may be configured to accumulate the scores for the PFOI that are located upstream of the first select location 904 along a first venous pathway 906 associated with reaching the first select location 904 when implanting the lead at an upstream origination site 908 off of the coronary sinus 910. In FIG. 9, the three scores associated with PFOI between the first select location 904 and the upstream origination site 908 are +3, +3, and +2, so the aggregated total value for the first selected location 904 is 8. The total value for the selected location 904 may be displayed on or next to the venous map 900, along with any other user-selected locations. Optionally, the workstation 110 may be configured to allow a user, such as a physician, to view both venous map 800 (shown in FIG. 8) and venous map 900 simultaneously or consecutively by switching between viewing and/or scoring modes.

Alternatively or additionally, an aggregated score could be summed for each coronary vein that branches off from the coronary sinus. The veins may be identified automatically using image processing, or the user may select one or more veins of interest to view aggregated scores for those selected veins. In an embodiment, assigning scores to the PFOI based on at least one of predetermined feature-complexity relations or physician-entered complexity updates may be performed by one or both of the operations 408 and 410.

Referring back to FIG. 4, at 412, operation tools, leads, and/or steps likely to be successful in the medical lead implant procedure are determined based on the scores. Some delivery tools that may be used in a medical lead implantation procedure include outer catheters (e.g., sheaths), inner catheters (e.g., sub selectors), and guidewires. Some types of leads that may be used include unipolar, bipolar, quadripolar leads, or leads having different amounts of pacing electrodes. Leads also may be classified based on other characteristics, such as length, diameter, hardness, shape, materials, or the like. The determination may be based on a standard database of procedure history and/or the physician's own record. In an embodiment, the scoring circuit module 638 or other circuitry in the microcontroller 602 of the workstation 110 (shown in FIG. 2) may retrieve the operation tools, leads, and/or steps from the surgical planning database and/or a physician-specific surgical history. The determination may be based on the summed scores for the potential lead routes, and a separate determination may be made for each potential route or each selected route. Optionally, a separate determination may be made for scores that account for TVF and scores that do not account for TVF.

For example, regarding a potential stimulus site that has a relatively low score that indicates the site would be relatively easy to access with a medical lead, it may be determined that using a basic outer catheter or the physician's tool of choice would provide the best chance for a successful outcome during surgery (e.g., low procedure time and no complications). However, for a site with a total point value of 5 or more, for example, it may be determined that a tool designed for more complex procedures, such as a subselector (e.g., inner catheter), should be used, and/or the physician should take a retrograde, buddy wire approach. As stated above, the determinations of tools, leads, steps, and/or other planning information may be dependent on the computed total values (e.g., total scores) as correlated by a surgical planning database and/or a physician-specific surgical history.

At 414, the determined tools, leads, and/or steps are suggested to the user as treatment planning information. In an embodiment, the treatment planning information is displayed to the physician visually on the display 614 of the workstation 110 of the PG system 200 (shown in FIG. 2). Optionally, the treatment planning information may be audibly provided to the physician using the speaker 644 of the workstation 110. The treatment planning information provided to the physician also includes the scored lead routes and/or stimulus sites, or at least information about how the scores of the routes/sites compare. Thus, the physician is provided information about the accessibility of locating an electrode of a cardiac medical lead at one or more potential stimulus sites, such as a ranking of the most to least accessible potential stimulus sites. For example, the venous map may highlight one or more suggested lead routes and/or stimulus sites in the displayed map that are determined to have the best chance of success.

Optionally, the illustrated suggested paths may differ based on user-selected preferences. For example, the physician may select a favorite tool and/or type of lead, and the PG system 200 may display a suggested lead route and/or stimulus site based on performing the implant procedure using that tool and/or lead. In addition, a different route and/or site may be suggested based on whether or not TVF (e.g., dynamic changes over time to the venous pathways) are taken into account. Optionally, different routes and/or sites based on user-preferences may be displayed simultaneously, such as showing both a suggested route based on using a user-selected tool and simultaneously showing a suggested route based on using the best available tool as determined by the PG system 200.

In addition, the physician may be provided with information, such as suggested implant tools and/or medical leads to use and/or steps to follow, that is specific to the potential stimulus sites. Therefore, for a selected region or potential stimulus site, the physician may be presented with accessibility information as well as suggested tools and methods or steps to follow to increase the probability of a successful implantation procedure. The physician may use this provided treatment planning information that is patient-specific when planning for the surgery, such that during the procedure, the physician may introduce the medical lead along a chosen one of the venous pathways for the heart based on the treatment planning information.

At 416, the venous map may be projected onto images prior to and/or during the medical lead implant procedure. The images may be pre-acquired anatomical, electrical, or functional information related to the heart. For example, the venous scores may be overlaid with other maps used for planning CRT implantation. The venous map, for example, may be combined with an echo-recommended activation map that displays one or more late activation sites. Late activation sites refer to stimulus sites where a detected response to a pacing pulse is late (e.g., conduction delay is long) relative to other potential activation sites. Pacing from a site of late activation may produce a better acute hemodynamic response than pacing from an early activation site, which may improve the clinical outcome in patients undergoing CRT. Thus, by combining the venous map which shows preferred stimulus sites based on accessibility with the activation map which shows preferred stimulus sites based on activation time, the user is able to compare the maps. The user may weigh the tradeoff between placing the lead at the site of latest activation and placing the lead at the site that is easiest to reach, and the user may select a compromise site.

During the medical lead implant procedure, the venous map containing the treatment planning information may be used in conjunction with intraoperative imaging devices. For example, the venous map may be a 3D map that is projected or overlaid onto 2D images. The images may be live intraoperative fluoroscopy or ultrasound images. Alternatively, the images may be pre-recorded fluoroscopy images that are continuously looped over time in guidance technology such as MediGuide™ from St. Jude Medical Inc. The venous map may be registered or aligned to the patient's chest, such as by using markers on the acromia or xiphisternum of the patient, or aligned to implanted leads in the right ventricle and/or right atrium. Then, a right anterior oblique (RAO) and/or left anterior oblique (LAO) projection of the scored venous map may be made and placed over the live or MediGuide™-looped fluoroscopic images.

In an embodiment, the intraoperative images may be used to update and/or augment the venous map. For example, once the venous map is updated based on newly-acquired intraoperative image data, the PG system 200 may be configured to re-perform the operations (e.g., operations 404-414) of process 400 shown in FIG. 4. Thus, the treatment planning information that the PG system 200 provides may be updated during the lead implantation procedure, and not only prior to the start of the procedure.

In an alternative embodiment, the image data used to map the veins of the venous system is only obtained intraoperatively, and no images of the patient are obtained prior to the lead implant procedure. For example, the physician may start the procedure using physician-selected tools, leads, and methods, and may use a generic template that is not patient-specific as a guide. Image data may be obtained during the procedure, such as if the physician uses an IVUS catheter. The PG system 200 may obtain the captured image data and build the venous map intraoperatively, in addition to performing the processing steps to score identified PFOI. Optionally, the PG system 200 may still provide suggested treatment planning information, even though the procedure has already begun.

At 418, the results of the procedure are documented. For example, at the end of the procedure, the physician or nurse may record the final stimulus site (e.g., the final location of the stimulation electrode) or sites, the final lead route traversed by the lead, the type of lead implanted, and/or which tools and/or steps were used to maneuver the lead along the final lead route. Optionally, the final lead route traversed by the lead may be tracked automatically instead of manually by tracking the path traversed by a tip of the implant tool using a known automatic tracking system. In addition, observations about the surgery, such as whether the tools, leads, and/or steps used were successful or unsuccessful and the physician's preferred choices for tools, leads, and/or implant steps, may also be recorded to be used for reference when planning for future lead implant procedures.

This information updates the data in the PG system 200, such as information stored in the database 104 (shown in FIG. 1) and/or in internal memory within the user workstation 110 (shown in FIG. 2). For example, observations and records from a physician-specific surgical history may be used to provide treatment planning information for future implant procedures of the physician. Optionally, updates to the physician-specific history may be added to a surgical planning database or may be kept separately from the more general surgical planning database. In the latter case, the workstation 110 may be configured to retrieve treatment planning information from the physician-specific surgical history instead of or in addition to the surgical planning database whenever the information that is to be retrieved conflicts or differs between the two sources. In an embodiment, over time, the map of successful outcomes and recommendations (e.g., tools, type of lead, implant steps, and the like) in connection with each potential stimulus site becomes tuned to the physician, instead of reflecting the standard database.

As mentioned above in the description of FIG. 7, the scoring scheme may also adapt to the physician's preferences and/or strengths and weaknesses. For example, if a physician updates a score assigned to a PFOI that has a 160 degree U-turn to decrease the score to +1 point because the physician never has trouble with 160 degree U-turns, then this update may be stored in the physician-specific surgical history. The scoring may be updated for this physician such that for future implant planning for an implantation procedure to be performed by this physician, identified PFOI having 160 degree U-turns will automatically be scored as +1 point. In an embodiment, the PG system 200 may be configured to include multiple physician-specific surgical history databases in order to customize the treatment planning information presented to each of multiple physicians that use the user workstation 110.

In addition to adapting to individual physicians, the PG system 200 may be configured to adapt to new tools, leads, and techniques that develop over time. For example, as new tools and leads become available, new steps or techniques enter practice, and/or professional standards or consensus statements change, the surgical planning database and/or physician-specific surgical history may be updated to include this new information. The new information may be used to redefine the scoring, such as the feature-complexity relations, and alter the suggested planning information (e.g., tools and leads to use, steps to follow, lead routes and/or stimulus sites to navigate, etc.). For example, a newly developed tool and/or newly-developed medical lead may reduce the difficulty in navigating the lead through a U-turn, so the feature-complexity relation for U-turn PFOI may be decreased from +3 to +2. Optionally, the new tool and/or new lead may be suggested in the treatment planning information when a U-turn is identified in the venous map.

One or more embodiments described herein may provide the technical effect of identifying and scoring of geometric features of interest in coronary veins. In addition, the scores may be aggregated to suggest how difficult a potential final lead location via a potential stimulus site will be to reach. Based on the (aggregated) scores, one or more embodiments may provide the technical effects of recommending tools, medical leads, and/or implant operations with the best chance of successful lead implantation for each region or venous pathway, based on records stored in a database. Furthermore, the system may continuously update the records to reflect a physician's personal history with each potential implant site, so the recommendations may be customized to the specific physician over time. The embodiments described herein may provide the technical effect of enabling users, such as physicians, to anticipate and accommodate anatomical challenges, adjust expectations and strategies of the implant procedure, and/or reduce procedure time and complication risk by bypassing tools, leads, and strategies that have a low chance of success.

It is to be understood that the above description is intended to be illustrative, and not restrictive. For example, the above-described embodiments (and/or aspects thereof) may be used in combination with each other. In addition, many modifications may be made to adapt a particular situation or material to the subject matter of an embodiment described herein without departing from scope of the teachings herein. While the dimensions, types of materials and coatings described herein are intended to define parameters of one or more embodiments, they are by no means limiting and are exemplary embodiments. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms, "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for characterizing an accessibility of potential stimulus sites in connection with surgical planning for implant of a cardiac medical lead near a heart of a patient, the method comprising:
    obtaining image data representative of a coronary venous system for the heart of the patient to receive the lead;
    generating a venous map, based on the image data, representative of venous pathways for the heart of the patient;
    analyzing the venous map to identify pathway features of interest (PFOI) within at least one select region of the venous pathways;
    assigning scores to the PFOI based on at least one of predetermined feature-complexity relations or physician-entered complexity updates; and
    displaying treatment planning information to a user based on the scores, wherein the treatment planning information includes an identification of at least one of implant tools or a type of medical lead saved in a database as suggested to be used to locate an electrode of the medical lead at the corresponding stimulus site.

2. The method of claim 1, wherein the displaying operation is based on at least one of a surgical planning database or a physician-specific surgical history.

3. The method of claim 1, further comprising tabulating the scores for a plurality of PFOI at least one of within or upstream of the at least one select region of the venous pathways.

4. The method of claim 1, wherein the at least one select region is at least one of a pre-defined epicardial region, an identified coronary vein, or a user-selected location of the venous map.

5. The method of claim 1, further comprising introducing the medical lead along a chosen one of the venous pathways for the heart based on the treatment planning information.

6. The method of claim 1, wherein the analyzing operation includes identifying at least one of a location, tortuosity, angle, and diameter of potential geometric obstacles in the venous pathways as the PFOI.

7. The method of claim 1, wherein the analyzing operation includes identifying predetermined shapes within the venous pathways as the PFOI, the PFOI including at least one of branch bifurcations, acute angles, U-turn changes of direction, pathway narrowing, and overall tortuosity of a segment of the venous pathway.

8. The method of claim 1, further comprising assigning a total value to the at least one select region of the venous pathways, the total value representing risk weights associated with approaching the corresponding select region with the medical lead.

9. The method of claim 1, further comprising providing a user interface configured to permit the user to designate a first select location, and displaying a total value determine in connection with the first select location, wherein the total value represents an aggregation of the scores for the PFOI that are located upstream of the first select location along a corresponding venous pathway located between the first select location and an upstream origination site.

10. The method of claim 1, wherein the treatment planning information further includes an identification implant steps that are suggested to be followed to locate an electrode of the medical lead at the corresponding stimulus site.

11. The method of claim 1, wherein the treatment planning information further includes a comparative representation of the projected accessibility of the potential stimulus sites, the comparative representation displayed as at least one of a color-based heat map or an integer-based map.

12. A procedure guidance (PG) system for characterizing an accessibility of potential stimulus sites in connection with surgical planning for implant of a cardiac medical lead near a heart of a patient, the PG system comprising:
- an imaging device configured to obtain image data representative of a coronary venous system for the heart of the patient to receive the lead;
- a venous map circuit module configured to generate a venous map, based on the image data, representative of venous pathways for the heart of the patient;
- a pathway features of interest (PFOI) identification circuit module configured to analyze the venous map to identify PFOI within at least one select region of the venous pathways;
- a scoring circuit module configured to assign scores to the PFOI based on at least one of predetermined feature-complexity relations or physician-entered complexity updates; and
- a display device configured to provide treatment planning information to a user based on the scores, wherein the treatment planning information includes an identification of at least one of implant tools or a type of medical lead saved in a database as suggested to be used to locate an electrode of the medical lead at the corresponding stimulus site.

13. The PG system of claim 12, wherein the imaging device obtains at least one of MRI, CT, fluoroscopy, or ultrasound images of the heart.

14. The PG system of claim 12, wherein the venous map circuit module performs an automated segmentation analysis of the image data to form the venous map.

15. The PG system of claim 12, wherein the scoring circuit module aggregates the scores associated with the PFOI along corresponding venous pathways located between the potential stimulus sites and potential upstream origination sites to determine a total value for each of the corresponding venous pathways, the display device displays the total value associated with at least one of the venous pathways.

16. The PG system of claim 12, wherein the treatment planning information includes an identification of implant tools, a type of medical lead, and an identification of implant steps saved in a database as suggested to be used or followed to locate an electrode of the medical lead at the corresponding stimulus site.

17. The PG system of claim 12, wherein the treatment planning information further includes an identification of implant steps saved in a database as suggested to be followed to locate an electrode of the medical lead at the corresponding stimulus site.

18. The PG system of claim 12, wherein the display device displays the treatment planning information overlaid onto an image of the heart, the image including at least one of pre-acquired anatomical, electrical, or functional information related to the heart.

19. The PG system of claim 12, wherein the treatment planning information is retrieved by the scoring circuit module from at least one of a surgical planning database or a physician-specific surgical history.

20. The PG system of claim 19, wherein the surgical planning database is updated after the implant of the medical lead with at least one of a final stimulus site, a final lead route, a type of medical lead implanted, a list of tools used to maneuver the lead along the final lead route, or a list of steps taken to maneuver the lead along the final lead route.

21. The PG system of claim 19, wherein the surgical planning database is updated after the implant of the medical lead with a physician's choices for at least one of tools, type of medical lead, or implant steps to form the physician-specific surgical history in connection with each potential stimulus site.

22. The PG system of claim 19, wherein at least one of the surgical planning database or the physician-specific surgical history is updated to include at least one of newly available tools, newly available medical leads, newly practiced steps, or newly determined feature-complexity relations.

* * * * *